United States Patent [19]

Höfer

[11] Patent Number: 5,318,295
[45] Date of Patent: Jun. 7, 1994

[54] GAME SCORE EVALUATION AND GAME CONTROL SYSTEM ON THE BASIS OF PLAYER'S PHYSICAL VALUES

[76] Inventor: Jürgen Höfer, Heidlohstrasse 2, 2000 Hamburg, Fed. Rep. of Germany

[21] Appl. No.: 901,243

[22] Filed: Jun. 19, 1992

Related U.S. Application Data

[63] Continuation-in-part of Ser. No. 573,033, Aug. 9, 1990, abandoned.

[30] Foreign Application Priority Data

| Feb. 9, 1988 | [DE] | Fed. Rep. of Germany | 3803884 |
| Feb. 16, 1988 | [DE] | Fed. Rep. of Germany | 3804746 |
| Mar. 28, 1988 | [DE] | Fed. Rep. of Germany | 3810530 |
| Apr. 12, 1988 | [DE] | Fed. Rep. of Germany | 3812079 |
| Apr. 19, 1988 | [DE] | Fed. Rep. of Germany | 3813032 |
| Oct. 12, 1988 | [DE] | Fed. Rep. of Germany | 3833630 |
| Oct. 12, 1988 | [DE] | Fed. Rep. of Germany | 3834746 |
| Oct. 21, 1988 | [DE] | Fed. Rep. of Germany | 3835813 |
| Nov. 2, 1988 | [DE] | Fed. Rep. of Germany | 3837164 |
| Nov. 25, 1988 | [DE] | Fed. Rep. of Germany | 3839774 |

[51] Int. Cl.$^5$ ............................ A63F 7/00; A61B 5/08
[52] U.S. Cl. .......................... 273/118 A; 273/85 G; 273/434; 273/118 R; 128/718; 128/719; 128/632
[58] Field of Search ............ 273/108 R, 118 R, 118 A, 273/85 G, 148 B, 434; 128/718, 719, 632, 633, 634, 732

[56] References Cited

U.S. PATENT DOCUMENTS

| 3,799,149 | 3/1974 | Rummel et al. | 128/718 |
| 3,826,250 | 7/1974 | Adams | 128/24.2 |
| 3,855,998 | 12/1974 | Hidalgo-Briceno | 128/732 |
| 3,895,630 | 7/1975 | Bachman | 128/718 |
| 4,149,716 | 4/1979 | Scudder | 273/85 G X |
| 4,162,793 | 7/1979 | Cummings | 273/121 A |
| 4,368,740 | 1/1983 | Binder | 128/718 |
| 4,463,764 | 8/1984 | Anderson et al. | 128/718 |
| 4,485,822 | 12/1984 | O'Connor | 128/719 |
| 4,553,748 | 11/1985 | Allen et al. | 273/434 |
| 4,724,845 | 2/1988 | Callahan | 128/718 |
| 4,753,245 | 6/1988 | Gedeon | 128/718 |

FOREIGN PATENT DOCUMENTS

| 0076125 | 4/1983 | European Pat. Off. |
| 0177075 | 4/1986 | European Pat. Off. ........ 273/148 B |
| 8601317 | 2/1986 | World Int. Prop. O. ........ 273/85 G |
| 8800480 | 1/1988 | World Int. Prop. O. |

*Primary Examiner*—Vincent Millin
*Assistant Examiner*—Raleigh W. Chiu
*Attorney, Agent, or Firm*—Michael J. Striker

[57] ABSTRACT

A skill-testing, entertainment or game equipment operating on the basis of user's physical values comprises units for non-invasive measuring physical values of a user, a computer unit arranged to receive the physical values of a user measured by the measuring units, the normal game score of the equipment and also to receive multiplication factors for certain physical values and units for displaying the scores produced by multiplication of the physical values measured by the measuring units or game scores with the multiplication factors supplied to the computer unit.

18 Claims, 4 Drawing Sheets

FIG. 1
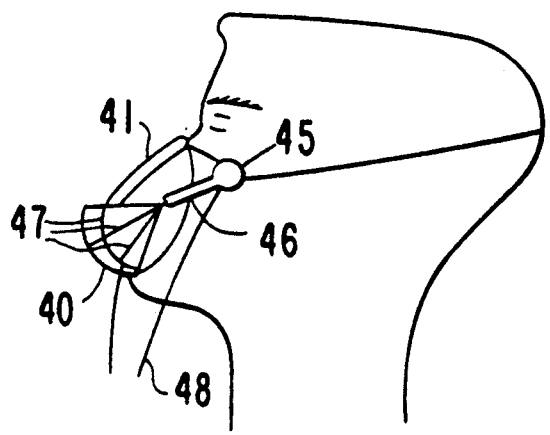
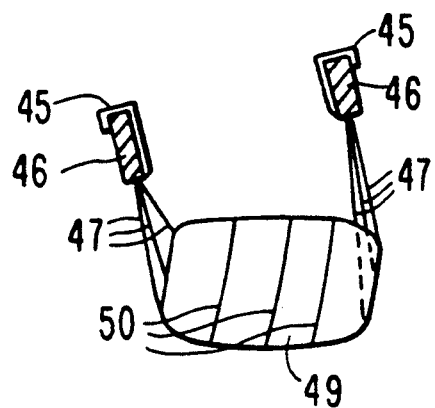
FIG. 2
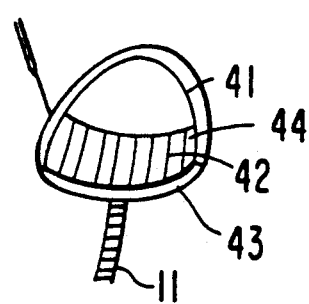
FIG. 3

GAME SCORE EVALUATION AND GAME CONTROL SYSTEM ON THE BASIS OF PLAYER'S PHYSICAL VALUES

CROSS-REFERENCE TO RELATED APPLICATIONS

This application is a continuation-in-part of U.S. application Ser. No. 573,033 filed Aug. 9, 1990, abandoned.

A continuation application Ser. No. 08/158,760 containing claims of a scope different from the scope of the claims of the present application Ser. No. 901,243, has been filed.

BACKGROUND OF THE INVENTION

The present invention relates to an electronic or electro-mechanical skill-testing, entertainment or game equipment—such as for instance video games, pinball machines or skill-testing game machines or the like— with a system of controlling this equipment and/or for evaluation of the test or game results obtained with the equipment dependent on physical values of a person.

It is known to measure non-invasively some physical values of users. For example, a non-invasive measurement of blood gas values, such as blood oxygen value or blood carbon dioxide value can be performed by an electro-chemical sensor. The measuring contact surface of the sensor is warmed up to approximately 43° C. and located above the skin of any part of the body. The warmed up sensor contact surface is causing a local arterialization of the skin. The part of the skin which is in contact with the sensor is furthermore covered with a chemical, whereby the value of the blood gas diffusing through the skin into the chemical is measured by the electro-chemical sensor with the help of measuring polarography instrument wired with the sensor.

It is also known to measure non-invasively saturation of the blood with certain blood gases such as for instance with blood oxygen or with blood carbon dioxide by a photometric sensor. This sensor emits light with different wave lengths. The light penetrates blood and tissue and is partly absorbed and modulated dependent on the degree of saturation of the blood with blood gases. The modulated light is received by the detector of the sensor which measures the blood gas value with a measuring instrument evaluating the extent of the modulation and wired with the sensor. Also, so-called oximeter sensors can take measurements of both blood oxygen and pulse rate values at the same time by the photoelectric method. Furthermore a large number of measuring means are known and mentioned in the following, which enable non-invasive measuring physical values of a user completely painless and bloodless and without the necessity of a surgical treatment.

Furthermore, biofeedback devices are known which have stimulus generating means for applying some physical or chemical stimulus to an individual's body and means for measuring the reaction from an individual's body in response to said stimulus.

The above-mentioned methods have been almost exclusively used in intensive care units and other situations, for medical diagnostics and the like.

SUMMARY OF THE INVENTION

Accordingly, it is an object of the present invention to provide a procedure and an equipment which can attract many people by using skill-testing, entertainment or game equipment so that the people will be enabled to gain playfully knowledge of their physical conditions and their reaction to the effects of the equipment. The use of such procedure and equipment can be above all, but not exclusively, for the purpose of entertainment and amusement of the public.

In keeping with these objects and with others which will become apparent hereinafter, one feature of the present invention resides, briefly stated, in a skill-testing, entertainment or game equipment operating on the basis of user's physical values, which has measuring means in current use for non-invasive measuring physical values of a user completely painless and bloodless and without the necessity of a surgical treatment, operating for example on the basis of electro-chemical or photoelectric or ultrasonic measurements; or on the basis of measuring an electric current or the electric resistance or the temperature of the skin or the skin moisture or muscle activities of a user; or on the basis of measuring the content of alcohol or of any gases in the exhaled breath of a user; a computer unit arranged to receive the normal score and the physical values of a user measured by said measuring means and also to receive multiplication factors for certain physical values and means for displaying scores, such as for instance an electro-mechanical or electronic display, for the display of certain evaluated scores, as detailed in the following embodiment.

Further examples for commercially available means realizing some of the above measurements of physical values are dermaohmmeter, dermathermometer, electroencephalograph, hygrometer and amperemeter. These instruments can be positioned within the game equipment or outside of same. The measuring electrodes or sensors of these instruments are set on the body of a player or they are mounted in the game equipment. It would, for example, be possible to realize the installation of said electrodes or sensors in contact surfaces of the game equipment, preferably in places which are in frequent contact with the hands of the player.

When the equipment is designed in accordance with the present invention, it achieves the above-mentioned objectives.

In accordance with another feature of the present invention, the equipment is provided with a display field for displaying the measured physical values.

In accordance with another feature of the present invention, the equipment is provided with stimulus generating means for applying some physical or chemical stimulus to the player's body. Examples for stimulus generating means are microwave radiators, infrared radiators, vibrations or current impulses producing means, fans or blowers producing a cooling airflow and other various physical and chemical stimulating means.

Also, controlling means can be provided and connected with the computer unit or directly with the measuring means, so as to turn the skill-testing, entertainment or game equipment—if necessary only functional or decorative parts of same—on and off, or to change intensity of current supplied to the said equipment—or to certain parts of same, or to transmit an enabling pulse to said stimulus generating means, or to a certain game unit in common use in game machines, such as for instance add unit, substract unit, game processing unit or other appropriate game units, so as to enable by this pulse—if the pulse is transmitted to an add unit or a subtract unit—for instance the addition or deduction of a certain kind of score or bonus, such as for example a certain number of points or lives of game figures or portions of fighting energy, or extra rounds, balls or games, or continues; or—in case the pulse is transmitted to a processing unit or appropriate other known games units—the actuation of certain game activities, such as for example a certain game action, a certain sequence of game actions, a certain game speed or the appearance in the game of a certain game figure with certain abilities, or the like.

Preferred embodiments of the invention are those explained in the following:

In the case of one embodiment the player becomes active himself and activates certain functions of the equipment. In the case of another embodiment, however, he only observes the actions of the equipment without becoming active himself.

In the case of one embodiment the player will receive a certain score for his performance. A computer unit is arranged to receive the physical values of a user measured by means for non-invasive measuring and also to receive the normal score of the skill-testing, entertainment or game equipment and certain multiplication factors for certain physical values. The normal score is evaluated in dependence on one or more physical values of the user, and consequently the evaluated score produced by multiplication of the normal score of the equipment with the multiplication factors resulting from the physical values is displayed on means for displaying scores.

In the case of a modification of this embodiment the user can effect any kind of control—in dependence on one or more physical values and under consideration of the obtained normal score—upon the equipment. Also in this case the physical value is measured non-invasively and a computer unit as afore-mentioned is arranged. Furthermore, controlling means are connected with said computer unit. The controlling means receive from said computer unit the evaluated score produced by multiplication of the normal score of the equipment with the multiplication factors resulting from the physical values. The controlling means are programmed to turn any functional or only decorative part of the skill-testing, entertainment or game equipment on or off, or to change the intensity of current supplied to the equipment, or to provide an enabling pulse to stimulus generating means or certain game units in common use in game machines, in dependence on certain evaluated scores received by the controlling means from said computer unit. The controlling means are programmed so as to effect said switchings or changes of current intensity or transmissions of pulses to the stimulus generating means or to certain known game units, effecting certain game activities, in the moment when certain evaluated scores are received from the computer unit.

In the case of another modification of this embodiment the controlling means are programmed to effect said switchings or changes of current intensity or transmissions of pulses to stimulus generating means or to certain known game units in the moment when the value of the difference between at least two scores resulting from the above-mentioned multiplications and received from the computer unit coincides with a certain value, which has been supplied to the controlling means earlier.

In case of another embodiment the user only observes the action on the equipment. The user obtains a score only in dependence on any physical value measured on him, but without consideration of his playing performance. In this case a skill-testing, entertainment or game equipment is comprising means for non-invasive measuring physical values of a user. A computer unit is arranged to receive the physical values measured by said measuring means and also to receive multiplication factors for certain physical values; and means for displaying the scores produced by multiplication of the physical values with the multiplication factors supplied to said computer unit for each physical value.

In case of a modification of this embodiment the user is effecting a certain control of the equipment only in dependence on any physical value measured on him, but without consideration of his playing performance. In this case a skill-testing, entertainment or game equipment is comprising means for non-invasive measuring physical values of a user. A computer unit is arranged to receive the physical value measured by said measuring means and also to receive certain multiplication factors for certain physical values. Furthermore controlling means are connected with said computer unit. The controlling means receive from said computer unit the scores produced by multiplication of the physical values with the multiplication factors supplied to said computer unit for each physical value. The controlling means are programmed to turn the skill-testing, entertainment or game equipment or only any functional or decorative part of it on or off, or to change the intensity of current supplied to the equipment or to parts of it, or to provide an enabling pulse to stimulus generating means or to a certain game unit in common use in game machines, in dependence on certain scores received by the controlling means from the computer unit, whereby these scores have been produced as afore-mentioned by multiplication of the physical values with the multiplication factors supplied to said computer unit.

In the case of another modification of this embodiment the controlling means are programmed to effect said switchings or changes of current intensity or transmissions of pulses in the moment when the value of the difference between at least two measured physical values received from the computer unit coincides with a certain value, which has been earlier supplied to the controlling means.

The measuring means can measure an physical values such as for example a blood gas value, a pulse rate value of the user, etc.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIGS. 1-3 are a views showing a special oxygen breathing mask or an equipment in accordance with the present invention, operating on the basis of blood oxygen values;

DESCRIPTION OF THE PREFERRED EMBODIMENTS

Figure 4:
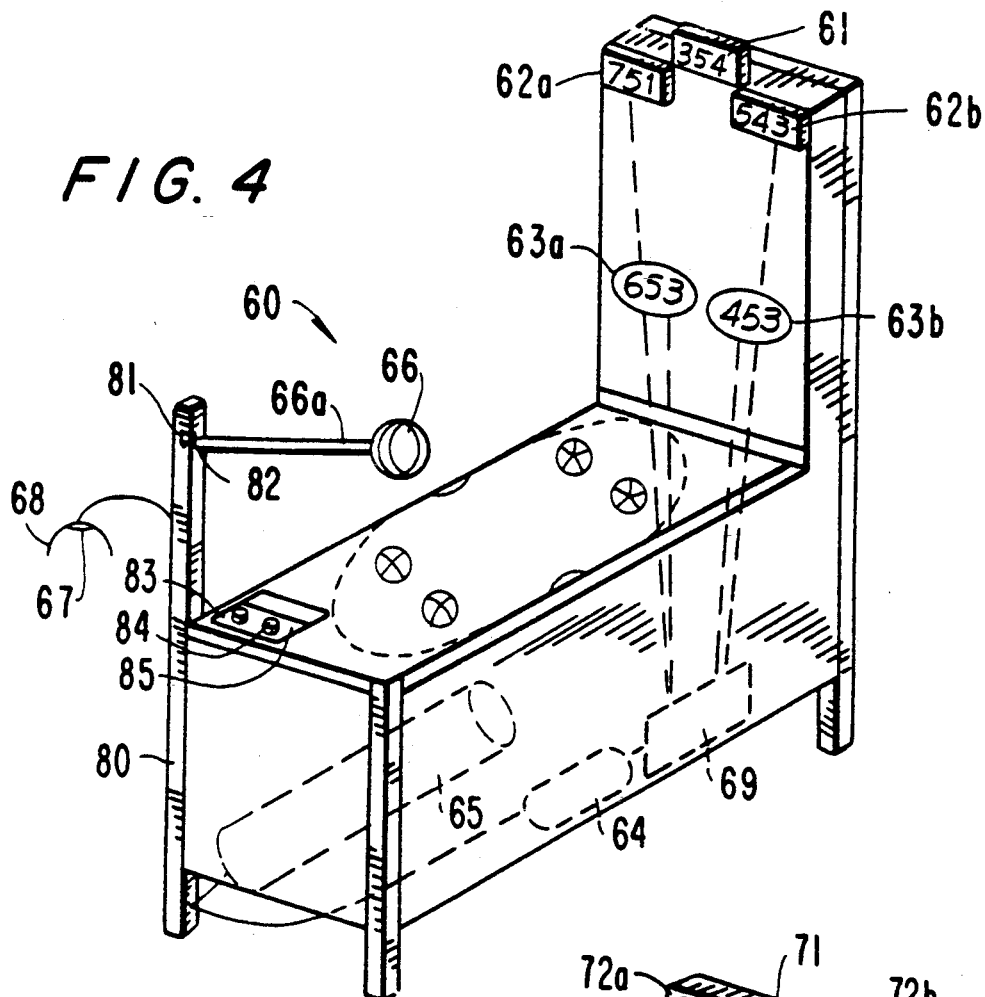
FIGS. 4 and 5 are views showing constructions of slot machines and entertainment devices in accordance with the present invention.

In FIGS. 1-3 an oxygen mask 40—applicable for the invention—is shown, which is designed so that its upper part 41 looks like a usual $O_2$, ask (i.e. made of non-porous material e.g. of plastic or rubber) while its lower part 42 is perforated with any kind (e.g. round, long or other types) of holes 44 so that normal breathing of room air is possible, in comfort. At the pouch 43 of the mask 40 the lower part of a thin, closed—air or $O_2$ tight—plastic or rubber sheath 49 is fastened which is connected on both sides with two pulling devices 46 activated by small electric motors by means of thin, elastic wire or several small bands 47 which can be thread or string. The electric motors and pulling device are fastened to the upper part of 41 of to the $O_2$ mask 40. The electric motor 45 is activated via wiring 48 (which also serves for current supply) by the device for transcutaneous measurement of the $pO_2$ at the moment when opening of the $O_2$ inlet value—also released by impulse from this device—takes place and thus the supply of pure $O_2$ or of air with increased $O_2$ content is initiated. Hereby the plastic or rubber sheath 49—which is somewhat larger than the lower part 42 of the $O_2$ mask 40—is pulled with wires or bands 47 until the skin 49 has positioned itself firmly onto the lower part 42 of the $O_2$ mask, whereby a small part of the upper part 41 of the $O_2$ mask is also sealed off so that no further intake of room air or $O_2$ is possible. At this moment the pulling device 46 locks so that the wires or bands 47 fix the sheath 49 over the $O_2$ mask.

As soon as the supply of pure $O_2$ or of air with increased $O_2$ content is interrupted by means of impulse of the device for transcutaneous measurement of the $pO_2$, the lock is released by means of an impulse transferred via wiring 48 and the electric motor 45 is activated. By way of the pulling device 46 this results in a slackening of the holding wires or belts 47 so that the sheath 49 exposes the perforations 44 for subsequent breathing of room air. To guarantee the troublefree sealing off of the lower part 42 of the mask 40, the sheath 49 is reinforced with a number of thicker struts 50 (plastic or rubber) which prevent the sheath from folding together.

Figure 5:
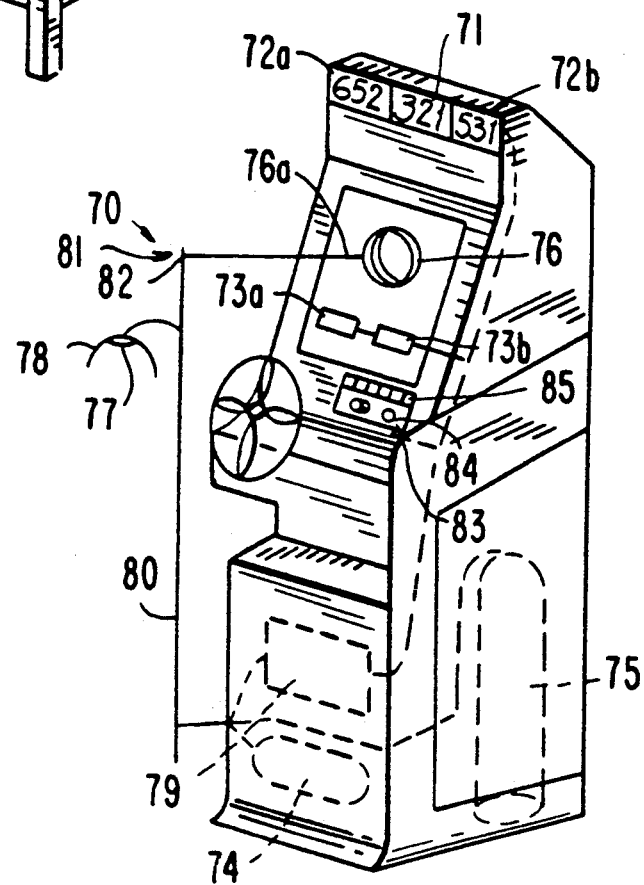

In FIGS. 4 and 5 special designs for gambling or skill-testing devices are shown. In FIG. 4 a pinball machine and in FIG. 5 a skill-testing device. The shown arrangement can be applied however to any entertainment apparatus with which tasks have to be solved and/or activities have to be performed which require physical strength, dexterity, quick reactions, a good eye-hand coordination of movements with good optical or acoustic perception, etc.

In order to provide the familiar games or devices 60; 70 with the oxygen supply apparatus, an additional, detachable or concealable display field 61; 1 for the blood oxygen value and an extra display field 62a; 72a for the increased or reduced values and an extra display field 62b; 72b for a second player (both also detachable or concealable) are installed in the area of the usual display of game or test scores 63a; 63b; 73a, 73b.

Furthermore a device 64; 74 for non-invasive measurement of the oxygen value is installed within the apparatus 60; 70 which is connected with a computer unit 69; 79 and via corresponding wiring with a cuff 68; 78 with incorporated sensor 67; 77 of the apparatus 64, 74/ In addition an oxygen cylinder 65; 75 is installed in the apparatus 60; 70 as oxygen source (alternatively, a central $O_2$ source is also possible) which is connected to the oxygen mask 66; 76 via a tube 65a; 75a fastened to a swivel-mounted and vertically adjustable support 80. In the tubing 65a; 75a (not shown in the drawing) from the oxygen source to the oxygen mask 66; 76, a control valve 81 is installed. It opens and closes around a horizontal and/or vertical axis dependent on the adjusting movement of the support 80. The support 80 is fixable via an outlined locking device 82 in an opened position of the valve 81.

The control of the device 60; 70 and/or score evaluation depending on the oxygen value is done via a computer unit 69; 79 connected with the device 64; 74 for non-invasive measurement of the oxygen value and to the display fields 61; 71, 62; 72a, 62b; 72b or alternatively 63a, 73a' 63b, 73b—which can be designed as any alphanumeric display—to the control valve 81, to a keyboard, to an input field 83 with pushbuttons or pressure switches 84 and to the not shown control device of the apparatus 60; 70. The oxygen values or alternatively multiplicators for certain oxygen values out in or preselected via the input field 83 are shown in the additional display field 85.

Figure 6:
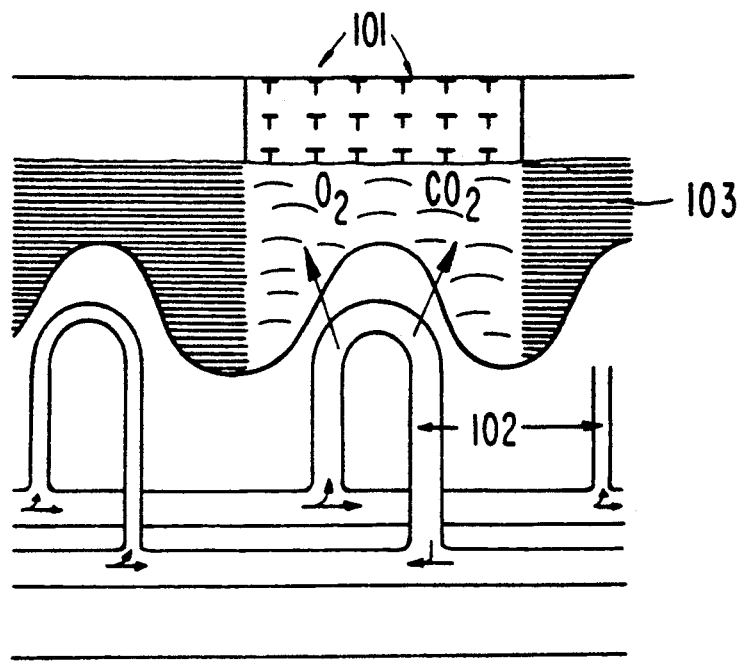
FIG. 6 is a view showing a sensor of the equipment in accordance with the present invention for determining carbon dioxide blood values of the user, for operating the equipment.

It is to be understood that physical values can be used for operating the inventive equipment. One of such values is for example blood carbon dioxide value. In order to use the blood carbon dioxide value for operating the equipment a sensor 101 is provided as shown in FIG. 6. As specified hereinabove, the sensor 101 can be an electro-chemical sensor with a contact surface warming to approximately 43° C. and located above the skin to cause a local arterialization of the skin which is covered with a chemical. The value of the blood gas diffusing through the skin into the chemical is measured by electro-chemical sensor with the help of the measuring polarography instrument wired with the sensor. FIG. 6 illustrates vasodilation of capillary 102 resulting in increased blood flow and disorganization of lipid structures of the epidermis 103 due to the heating effects of the sensor (electrode) 101. The result is blood gas ($O_2$ and $CO_2$) diffusion through the skin and to the blood carbon dioxide sensor 101. The sensor can be of another type, namely for measurements of saturation of the blood with carbon dioxide by a photometric method. Such a sensor emits light with different wave lengths, which penetrates blood and tissue and is partly absorbed and modulated depending on the degree of saturation of the blood with blood gases. The modulated light is received by a sensor detector and the degree of modulation is evaluated by an evaluating circuit.

Figure 7:
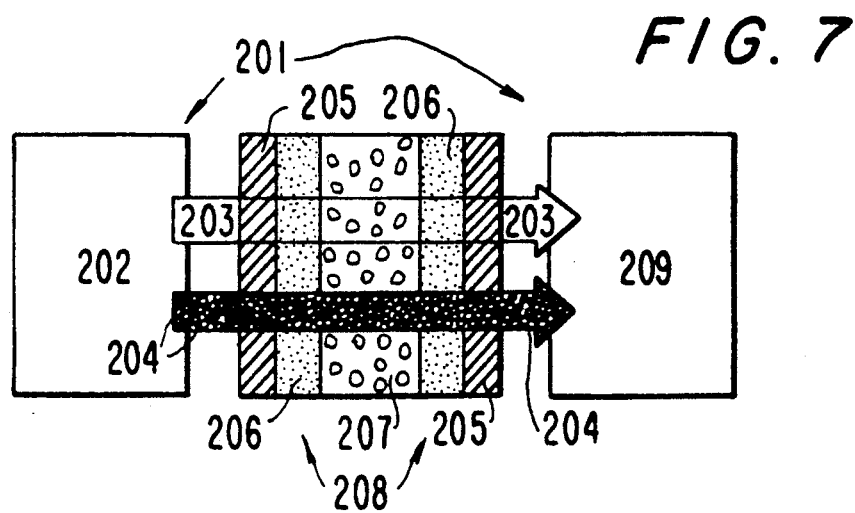
FIG. 7 is a view showing a pulse rate sensor for the inventive equipment so that the equipment operates on the basis of user's pulse rate values.

FIG. 7 shows a pulse rate sensor 201 provided in the equipment so that the equipment operates on the basis of the user's pulse rate. The pulse rate sensor can be of any type. It can be for example a so-called oximeter sensor 201 which determines a pulse rate value and at the same time i determines also blood oxygen values. This oximeter sensor 201 measures both saturation of the blood with oxygen and at the same time pulse rate with the photometric method. A light emitter 202 emits red light 203 and infrared light 204 which penetrates tissue 205, venous blood 206 and arterial blood 207 for instance of a finger 208. The emitted light is modulated depending on both degree of saturation of the blood with oxygen and pulsations. The modulated light is received by a sensor detector 209 and the degree of modulation is evaluated by an evaluating circuit. Such oximetersensor is produced by many companies, for instance in the United States by Criticare Systems, Inc., Milwaukee, Wis. 53226; Ohmeda, Louisville, Colo. 80027 and In-vivo Research Inc., Winter Park, Fla.

Figure 8:
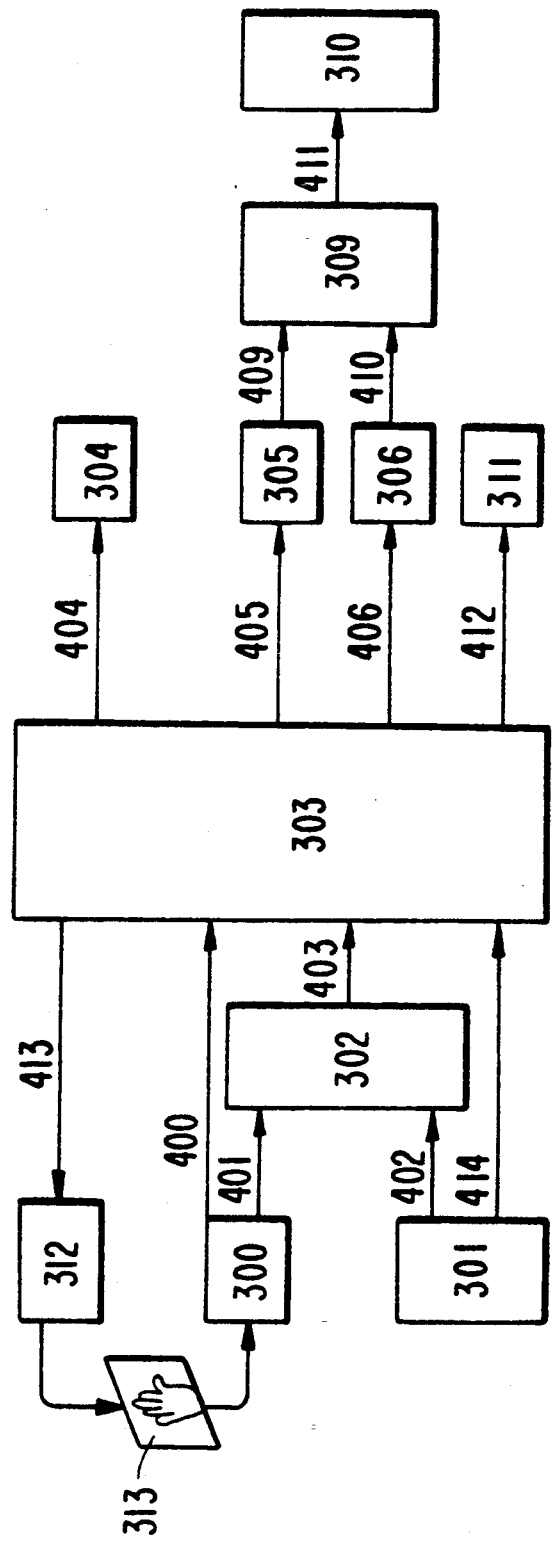
FIG. 8 is a block diagram of the control system according to the invention.

FIG. 8 shows a block diagram of the control system according to the invention. The different kinds of control of the skill-testing, entertainment and game equipment 304 (in the following called "equipment") or of parts of it in dependence on physical values of the user of the equipment will become apparent from this block diagram.

Essentially, the control of the equipment is effected by a control unit 303.

In case of a first embodiment this control unit 303 is arranged to receive physical values of a user over lead 400 directly from means for non-invasive measurements of physical values 300.

In case of a second embodiment the control unit 303 is arranged to receive from a computer unit 302 over lead 403 the score produced by multiplication of the physical values—measured by said measuring means 300 and transmitted to the computer unit 302 over lead 401 with the multiplication factors supplied to said computer unit 302 for the physical values.

In case of a third embodiment the control unit 303 is arranged to receive from a computer unit 302 over lead 403 the score produced by multiplication of the normal game score of the equipment, transmitted from any game scoring means 301—such as for instance the output of a score device switch, a game score register or a score encoder—over lead 402 to the computer unit 302, with the multiplication factors resulting from the physical values transmitted from the means for non-invasive measurements 300 over lead 401 to the computer unit 302.

In case of the second and third embodiment a certain multiplication factor is supplied to the computer unit 302 for each physical value.

Consequently, the control unit 303 is programmed to turn the game equipment 304 or parts of its over lead 404 on and off, or to change intensity of current supplied to the equipment 304 or parts of it over lead 404, or to provide an enabling pulse to the input of any game unit common in use—as described in detail in the following, either in case of the first embodiment only in dependence on physical values received from the mean for non-invasive measurements 300, or in case of the second embodiment independance on the score produced by multiplication of the physical values measured by said measuring means 300 with the multiplication factors supplied to said computer unit 302 for the physical values, or in case of the third embodiment in dependence on the score produced by multiplication of the normal score of the skill-testing, entertainment or game equipment with the multiplication factors resulting from the physical values.

All functional parts of the equipment are coupled to a suitable voltage source through an appropriate load register.

To enable the fourth and fifth embodiment of the invention, a detailed in the following, the control unit 303 has also register means enabling the storage of all physical values received from the means for non-invasive measurements 300 over lead 400, or the storage of all evaluated scores, resulting from above-mentioned multiplications, received from the computer unit 302 over lead 403. This storage being accomplished in registers internal to the control unit 303.

By computing means internal to the control unit 303, the control unit 303 is programmed to turn the equipment 304 on and off, or to change intensity of current supplied to the equipment 304, or to provide a pulse to the input of any game unit in common use in game machines—as described in detail in the following; either in case of a fourth embodiment in the moment when the value of the difference between at least two measurements of a physical value, figured out by the computing means, coincides with a certain value which has earlier been supplied to the computing means internal to the control unit 303; or in case of a fifth embodiment in the moment the value of the difference between at least two evaluated scores resulting from the above-mentioned multiplications—received over lead 403 from the computer unit 302 coincides with a certain value which has earlier been supplied to the computing means internal to the control unit 303.

In such aforementioned moments when the mentioned units in common use in game machines—such as for instance add unit 305, subtract unit 306 or a processing unit 311 or other appropriate equipment in common use in game machines enabling a certain game activity, such as for example the actuation of one certain game action of many possible game actions, or a certain sequence of game actions, or a certain game speed, or—especially in video games—the appearance in a game of a certain game figure with certain abilities—receive an enabling pulse, these known game units are energized and cause the said effects—if necessary with the help of other appropriate means known in game equipment.

In the event more than one of the mentioned known game units are connected to the control unit, computing means internal to the control unit 303 have the function to determine to which unit the enabling pulse shall be transmitted. This determination is accomplished by said computing means internal to the control unit 303 by comparing the physical value or evaluated score received by the control unit 303 with a value earlier supplied to same. In the moment said computing means compute by comparison of the received value with the value earlier supplied to same that the received physical value or evaluated score coincides with such a value or score earlier supplied to the control unit 303, which determines that an enabling pulse has to be transmitted to one certain known game unit—out of several connected game units, said computing means initialize that the control unit 303 transmits a pulse to said known game unit. Furthermore, in the moment said computing means determine—by comparison of the computed difference between at least two received physical values or evaluated scores with a value earlier supplied to same—that the computed difference coincides with a value earlier supplied to the control unit 303, which determines that an enabling pulse has to be transmitted to one certain known game unit, said computing means initialize that the control unit 303 transmits a pulse to said game unit. This means in other words that—in the event more than one of said game units are connected with the control unit 303—the computing means internal to the control unit 303 are programmed to select that an enabling pulse is transmitted to one certain known game unit—out of several connected known game units. This is done by comparison of the data received by the control unit 303 or of the computed difference between at least two received data with data earlier supplied to same which determine a pulse transmission to a certain known game unit.

In an add unit 305 a certain score or bonus, such as for example a certain number of points or lives of game figures or extra portions of fighting energy or similar are stored. In the moment a pulse is received from the control unit 303 by the add unit 305 over lead 405, the add unit 305 adds this certain score or bonus to a score or bonus register 309 over lead 409. As far as a display is desired, same is possible by display means 310 over lead 411.

In a subtract unit 306 a certain score or bonus as aforementioned is stored. In the moment a pulse is received from the control unit 303 by the substract unit 306 over lead 406, the subtract unit 306 deducts this certain score or bonus from a score or bonus register 309 over lead 410. As far as a display is desired, same is possible by display means 310.

By energizing over lead 412 a processing unit 311 or other appropriate game equipment in common use in game machines a certain game activity is released.

To enable the sixth embodiment of the invention, the control unit 303 is also connected over lead 413 with stimulus generating means 312. In this case the control unit 303 is programmed to transmit an enabling pulse to the input of the stimulus generating means 12 in the moment when normal scores received from the scoring means 301 over lead 414, or physical values received from said non-invasive measuring means 300 over lead 400, or scores received from the computer unit 302 resulting from the multiplications mentioned in the above second and third embodiment, or differences computed as mentioned in the above fourth and fifth embodiment coincide with data earlier supplied to the control unit 303. The energized stimulus generating means provide stimuli to parts of the body of the user 313.

It will be understood that each of the elements described above, or two or more together, may also find a useful application in other types of constructions differing from the types described above.

While the invention has been illustrated and described as embodied in a skill-testing, entertainment or game equipment, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. System for evaluation of the normal game score of any game equipment having game scoring means on basis of player's physical values, said game scoring evaluation system comprising: measuring means for non-invasive measuring of physical values of a player completely painless and bloodless and without the necessity of a surgical treatment, arranged to transmit measured physical values to a computer unit for producing evaluated scores; a computer unit arranged to receive any physical values of a player measured by said measuring means and to receive the normal game score from the game scoring means of said game equipment, and also to receive any multiplication factors for certain physical values, for the evaluation of said normal game score in dependence on physical values of a player, said evaluation to be effected by multiplication of said normal game score with said multiplication factors; game scoring means arranged to transmit the normal game score to said computer unit; any game equipment designed to enable a player to obtain a certain game score with his playing activities; and display means for displaying said scores evaluated by physical values of a player received from said computer unit, said measuring means being means for non-invasive measurements of blood oxygen values.

2. System for evaluation of the normal game score of any game equipment having game scoring means on basis of player's physical values, said game scoring evaluation system comprising: measuring means for non-invasive measuring of physical values of a player completely painless and bloodless and without the necessity of a surgical treatment, arranged to transmit measured physical values to a computer unit for producing evaluated scores; a computer unit arranged to receive any physical values of a player measured by said measuring means and to receive the normal game score from the game scoring means of said game equipment, and also to receive any multiplication factors for certain physical values, for the evaluation of said normal game score in dependence on physical values of a player, said evaluation to be effected by multiplication of said normal game score with said multiplication factors; game scoring means arranged to transmit the normal game score to said computer unit; any game equipment designed to enable a player to obtain a certain game score with his playing activities; and display means for displaying said scores evaluated by physical values of a player received from said computer unit, said measuring means being means for non-invasive measurements of pulse rate values.

3. System for the control of one of game, entertainment and skill-testing equipment operating on the basis of player's physical values, said control system comprising: measuring means for non-invasive measuring of physical values of a player completely painless and bloodless and without the necessity of a surgical treatment, arranged to transmit measured physical values to controlling means; controlling means arranged to receive physical values from said measuring means, programmed for at least one of turning one of game, entertainment and skill-testing equipment, and only a part of it on and off, changing intensity of current supplied to one of this equipment and a part of it, and putting any game units common in use in game machines into operation, in dependence on any desired physical values measured by said measuring means; one of game, entertainment and skill-testing equipment and known game units to be actuated by said controlling means, said known game units including adding and subtracting means for adding and deducting one of a desired score and bonus supplied to said adding and subtracting means, in response to actuation by said controlling means, to and from register means; and register means for receiving one of said added score and bonus, and from which one of said score and bonus is deducted.

4. System for the control of any game, entertainment and skill-testing equipment operating on the basis of player's physical value as defined in claim 3, including any stimulus generating means providing stimuli to a player in response to actuation by said controlling means.

5. System for the control of one of game, entertainment and skill-testing equipment operating on the basis of player's physical values, said control system comprising: measuring means for non-invasive measuring of physical values of a player completely painless and bloodless and without the necessity of a surgical treatment, arranged to transmit measured physical values to controlling means; controlling means arranged to receive physical values from said measuring means, programmed for at least one of turning one of game, entertainment and skill-testing equipment, and only a part of it on and off, changing intensity of current supplied to one of this equipment and a part of it, and putting any game units common in use in game machines into operation, in dependence on any desired physical values measured by said measuring means; one of game, entertainment and skill-testing equipment and known game units to be actuated by said controlling means, said known game units including game processing means programmed for producing, in response to actuation by said controlling means, one of a game speed and game activity.

6. System for the control of one of game, entertainment and skill-testing equipment operating on the basis of player's physical values, said control system comprising: measuring means for non-invasive measuring of physical values of a player completely painless and bloodless and without the necessity of a surgical treatment, arranged to transmit measured physical values to controlling means; a computer unit arranged to receive the physical values of a player measured by said measuring means and also to receive the normal game score of game, entertainment and skill-testing equipment from game scoring means and any desired multiplication factors for certain physical values, for evaluating said normal game score in dependence on physical values of a player by multiplication of said normal game score with said multiplication factors; game scoring means arranged to transmit the normal game score to said computer unit; controlling means connected with said computer unit, arranged to receive the scores evaluated in dependence on physical values from said computer unit, programmed for at least one of turning one of game, entertainment and skill-testing equipment, and only a part of it on and off, changing intensity of current supplied to this equipment and a part of it, and putting any game units common in use in game machines into operation, in dependence on any desired evaluated scores received from the computer unit; one of game, entertainment and skill-testing equipment and known game units to be actuated by said controlling means, said game units common in use in game machines including adding and subtracting means for adding and reducing one of a score and bonus supplied to said adding and subtracting means in response to actuation by said controlling means, to and from register means; and register means for receiving one of said added score and bonus, and from which one of said score and bonus is deducted.

7. System for the control of one of game, entertainment and skill-testing equipment operating on the basis of player's physical values, said control system comprising: measuring means for non-invasive measuring of physical values of a player completely painless and bloodless and without the necessity of a surgical treatment, arranged to transmit measured physical values to controlling means; a computer unit arranged to receive the physical values of a player measured by said measuring means and also to receive the normal game score of game, entertainment and skill-testing equipment from game scoring means and any desired multiplication factors for certain physical values, for evaluating said normal game score in dependence on physical values of a player by multiplication of said normal game score with said multiplication factors; game scoring means arranged to transmit the normal game score to said computer unit; controlling means connected with said computer unit, arranged to receive the scores evaluated in dependence on physical values from said computer unit, programmed for at least one of turning one of game, entertainment and skill-testing equipment, and only a part of it on and off, changing intensity of current supplied to this equipment and a part of it, and putting any game units common in use in game machines into operation, in dependence on any desired evaluated scores received from the computer unit; one of game, entertainment and skill-testing equipment and known game units to be actuated by said controlling means, said known game units including game processing means programmed for producing, in response to actuation by said controlling means, one of a game speed and game activity.

8. System for the control of one of game, entertainment and skill-testing equipment operating on the basis of player's physical values, said control system comprising: measuring means for non-invasive measuring of physical values of a player completely painless and bloodless and without the necessity of a surgical treatment, arranged to transmit measured physical values to controlling means; a computer unit arranged to receive the physical values of a player measured by said measuring means and also to receive the normal game score of game, entertainment and skill-testing equipment from game scoring means and any desired multiplication factors for certain physical values, for evaluating said normal game score in dependence on physical values of a player by multiplication of said normal game score with said multiplication factors; game scoring means arranged to transmit the normal game score to said computer unit; controlling means connected with said computer unit, arranged to receive the scores evaluated in dependence on physical values from said computer unit, programmed for at least one of turning one of game, entertainment and skill-testing equipment, and only a part of it on and off, changing intensity of current supplied to this equipment and a part of it, and putting any game units common in use in game machines into operation, in dependence on any desired evaluated scores received from the computer unit; one of game, entertainment and skill-testing equipment and known game units to be actuated by said controlling means; and any stimulus generating means providing stimuli to a player in response to actuation by said controlling means.

9. System for evaluation of the normal game score of any game equipment having game scoring means on the basis of player's physical values, said game scoring evaluation system comprising: measuring means for non-invasive measuring of physical values of a player completely painless and bloodless and without the necessity of a surgical treatment, arranged to transmit measured physical values to a computer unit for producing evaluated scores; a computer unit arranged to receive any physical values of a player measured by said measuring means and to receive the normal game score from the game scoring means of said game equipment, and also to receive any multiplication factors for certain physical values, for the evaluation of said normal game score in dependence on physical values of a player, said evaluation to be effected by multiplication of said normal game score with said multiplication factors; game scoring means arranged to transmit the normal game score to said computer unit; any game equipment designed to enable a player to obtain a certain game score with his playing activities; display means for displaying said scores evaluated by physical values of a player received from said computer unit, wherein said measuring means is means for measuring oxygen values of a user; and means for supplying oxygen to a user.

10. A game system, comprising a game equipment operative for providing playing activities and having a game scoring means enabling a player to obtain a normal score; measuring means operative for non-invasive measurement of physical values of a player and transmitting measured physical values; a computer unit arranged to receive the measured physical values from said measuring means, to receive the normal game scores from said game scoring means, and also to receive a multiplication factor for at least some physical values in a game so as to evaluate the normal game score in dependence on the physical values of a player with the use of multiplication of the normal game score with the multiplication factor; and display means for displaying the scores evaluated by the physical values received from said computer unit, said measuring means being means for non-invasive measurement of blood oxygen values.

11. A game system, comprising a game equipment operative for providing playing activities and having a game scoring means enabling a player to obtain a normal score; measuring means operative for non-invasive measurement of physical values of a player and transmitting measured physical values; a computer unit arranged to receive the measured physical values from said measuring means, to receive the normal game scores from said game scoring means, and also to receive a multiplication factor for at least some physical values in a game so as to evaluate the normal game score in dependence on the physical values of a player with the use of multiplication of the normal game score with the multiplication factor; and display means for displaying the scores evaluated by the physical values received from said computer unit, said measuring means being means for non-invasive measurement of pulse rate values.

12. A game system, comprising a game equipment operative for providing playing activities and having a game scoring means enabling a player to obtain a normal score; measuring means operative for non-invasive measurement of physical values of a player and transmitting measured physical values; a computer unit arranged to receive the measured physical values from said measuring means, to receive the normal game scores from said game scoring means, and also to receive a multiplication factor for at least some physical values in a game so as to evaluate the normal game score in dependence on the physical values of a player with the use of multiplication of the normal game score with the multiplication factor; display means for displaying the scores evaluated by the physical values received from said computer unit; and controlling means arranged to receive the measured physical values from said measuring means and operative for controlling said game equipment in dependence on any of the measured physical values, said controlling means being operative for turning on and off said game equipment.

13. A game system, comprising a game equipment operative for providing playing activities and having a game scoring means enabling a player to obtain a normal score; measuring means operative for non-invasive measurement of physical values of a player and transmitting measured physical values; a computer unit arranged to receive the measured physical values from said measuring means, to receive the normal game scores from said game scoring means, and also to receive a multiplication factor for at least some physical values in a game so as to evaluate the normal game score in dependence on the physical values of a player with the use of multiplication of the normal game score with the multiplication factor; and display means for displaying the scores evaluated by the physical values received from said computer unit, controlling means arranged to receive the measured physical values from said measuring means and operative for controlling said game equipment in dependence on any of the measured physical values, said controlling means being operative for turning on and off a part of said game equipment.

14. A game system, comprising a game equipment operative for providing playing activities and having a game scoring means enabling a player to obtain a normal score; measuring means operative for non-invasive measurement of physical values of a player and transmitting measured physical values; a computer unit arranged to receive the measured physical values from said measuring means, to receive the normal game scores from said game scoring means, and also to receive a multiplication factor for at least some physical values in a game so as to evaluate the normal game score in dependence on the physical values of a player with the use of multiplication of the normal game score with the multiplication factor; display means for displaying the scores evaluated by the physical values received from said computer unit; and controlling means arranged to receive the measured physical values from said measuring means and operative for controlling said game equipment in dependence on any of the measured physical values, said controlling means being operative for changing intensity of current supplied to said game equipment.

15. A game system, comprising a game equipment operative for providing playing activities and having a game scoring means enabling a player to obtain a normal score; measuring means operative for non-invasive measurement of physical values of a player and transmitting measured physical values; a computer unit arranged to receive the measured physical values from said measuring means, to receive the normal game scores from said game scoring means, and also to receive a multiplication factor for at least some physical values in a game so as to evaluate the normal game score in dependence on the physical values of a player with the use of multiplication of the normal game score with the multiplication factor; display means for displaying the scores evaluated by the physical values received from said computer unit; controlling means; and adding and subtracting means for adding and subtracting any desired score of said game equipment in response to actuation by said controlling means.

16. System as defined in claim 15, wherein said controlling means including register means for receiving the score to be added or substracted.

17. A game system, comprising a game equipment operative for providing playing activities and having a game scoring means enabling a player to obtain a normal score; measuring means operative for non-invasive measurement of physical values of a player and transmitting measured physical values; a computer unit arranged to receive the measured physical values from said measuring means, to receive the normal game scores from said game scoring means, and also to receive a multiplication factor for at least some physical values in a game so as to evaluate the normal game score in dependence on the physical values of a player with the use of mulitplication of the normal game score with the multiplication factor; display means for displaying the scores evaluated by the physical values received from said computer unit; controlling means; and processing means operative for producing one of a desired game speed and activity in response to actuation by said controlling means.

18. A game system, comprising a game equipment operative for providing playing activities and having a game scoring means enabling a player to obtain a normal score; measuring means operative for non-invasive measurement of physical values of a player and transmitting measured physical values; a computer unit arranged to receive the measured physical values from said measuring means, to receive the normal game scores from said game scoring means, and also to receive a multiplication factor for at least some physical values in a game so as to evaluate the normal game score in dependence on the physical values of a player with the use of multiplication of the normal game score with the multiplication factor; display means for displaying the scores evaluated by the physical values received from said computer unit; and controlling means operative for providing stimuli to the player in dependence on the normal game score and in response to actuation by said controlling means.

* * * * *